United States Patent [19]

Kiehs et al.

[11] 4,368,196

[45] Jan. 11, 1983

[54] PHOSPHORIC ACID ESTERS, AND THEIR USE FOR COMBATING PESTS

[75] Inventors: Karl Kiehs, Lampertheim; Heinrich Adolphi, Limburgerhof, both of Fed. Rep. of Germany

[73] Assignee: BASF Aktiengesellschaft, Fed. Rep. of Germany

[21] Appl. No.: 268,378

[22] Filed: May 29, 1981

[30] Foreign Application Priority Data

Jun. 2, 1980 [DE] Fed. Rep. of Germany ....... 3020897

[51] Int. Cl.³ .................. A01N 43/76; A01N 43/84; C07F 9/165; C07F 9/65
[52] U.S. Cl. .................................. 424/200; 260/944; 260/947; 424/216; 544/157; 548/112; 548/413
[58] Field of Search .............. 260/947, 944; 326.82; 424/216, 200; 544/157; 548/112

[56] References Cited

U.S. PATENT DOCUMENTS

| | | | |
|---|---|---|---|
| 2,802,855 | 8/1957 | Whetstone et al. | 260/943 |
| 2,908,605 | 10/1959 | Beriger et al. | 424/211 |
| 3,086,974 | 4/1963 | Schlor et al. | 260/944 |
| 4,127,654 | 11/1978 | Inoue et al. | 424/216 |

FOREIGN PATENT DOCUMENTS 1206425 12/1965 Fed. Rep. of Germany .

*Primary Examiner*—Anton H. Satto
*Attorney, Agent, or Firm*—Keil & Witherspoon

[57] ABSTRACT

Novel phosphoric acid esters of the formula

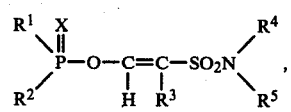

where $R^1$ is alkoxy of a maximum of 4 carbon atoms or phenyl, $R^2$ is alkyl of a maximum of 3 carbon atoms, alkoxy or alkylthio of a maximum of 4 carbon atoms, or alkylamino or dialkylamino, each alkyl being of a maximum of 4 carbon atoms, $R^3$ is methyl, ethyl, hydrogen or chlorine, $R^4$ and $R^5$ are phenyl or alkyl of a maximum of 4 carbon atoms, or are, together with the nitrogen atom, a 5- to 7-membered heterocycle, and X is oxygen or sulfur, with the proviso that $R^1$ is not phenyl when $R^2$ is alkyl. The compounds are suitable for combating pests.

4 Claims, No Drawings

PHOSPHORIC ACID ESTERS, AND THEIR USE FOR COMBATING PESTS

The present invention relates to novel phosphoric acid esters, processes for their manufacture, their use as pesticides, pesticides containing these phosphoric acid esters, a process for the manufacture of such agents, and a process for combating pests with these phosphoric acid esters.

U.S. Pat. No. 2,908,605 has already disclosed phosphates of carbamoylvinyl compounds, such as, for example, O,O-dimethyl-O-[(1-methyl-2-chloro-2,2-diethylcarbamoyl)-vinyl]-phosphate (also known as "phosphamidon"). However, the action of this compound in pest control is not always satisfactory.

We have now found that phosphoric acid esters of the formula

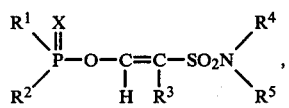

where $R^1$ is alkoxy of a maximum of 4 carbon atoms or phenyl, $R^2$ is alkyl of a maximum of 3 carbon atoms, alkoxy or alkylthio of a maximum of 4 carbon atoms, or alkylamino or dialkylamino, each alkyl being of a maximum of 4 carbon atoms, $R^3$ is methyl, ethyl, hydrogen or chlorine, $R^4$ and $R^5$ are phenyl or alkyl of a maximum of 4 carbon atoms, or are, together with the nitrogen atom, a 5- to 7-membered heterocycle, and X is oxygen or sulfur, with the proviso that $R^1$ is not phenyl when $R^2$ is alkyl, have an excellent insecticidal and acaricidal action.

Examples of alkoxy radicals for $R^1$ are methoxy, ethoxy, propoxy, isopropoxy, butoxy and isobutoxy; examples of alkyl, alkoxy or alkylthio for $R^2$ are methyl, ethyl, n-propyl, isopropyl, methoxy, ethoxy, n-propoxy, isopropoxy, n-butoxy, sec-butoxy, methylthio, ethylthio, n-propylthio, isopropylthio, n-butylthio, sec-butylthio and isobutylthio. Examples of alkylamino and dialkylamino for $R^2$ are methylamino, dimethylamino, ethylamino, diethylamino, methyl-ethylamino, diisopropylamino, n-butylamino and di-n-butylamino. Examples of alkyl for $R^4$ and $R^5$ are methyl, ethyl, propyl, isopropyl, butyl, and isobutyl. Examples of 5- to 7-membered heterocycles are pyrrolidine, morpholine, piperidine, and hexamethylenimine.

Preferred substituents for $R^1$ are methoxy, ethoxy, and phenyl; preferred substituents for $R^2$ are methoxy, ethoxy, n-propylthio, isobutylthio, sec-butylthio, methylamino, dimethylamino, and isopropylamino. $R^3$ is preferably hydrogen, chlorine or methyl. $R^4$ and $R^5$ are preferably methyl or ethyl, or form, with the nitrogen atom, a pyrrolidine or morpholine ring.

The novel phosphoric acid esters of the formula I may be prepared by reaction of a carbonyl compound of the formula

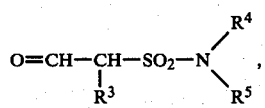

where $R^3$, $R^4$ and $R^5$ have the above meanings, with a phosphorus halide of the formula

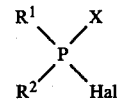

where $R^1$, $R^2$ and X have the above meanings and Hal denotes halogen.

The compounds II are in a state of equilibrium:

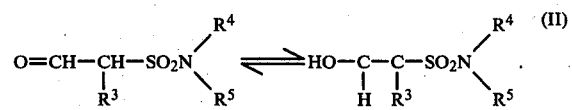

It is the enol form which reacts with the phosphorus halide III. The reaction of II with III proceeds well in the presence of acid acceptors, such as alkali metal hydroxides and carbonates, and aliphatic, aromatic or heterocyclic amines. The compounds II may also be reacted with II in the form of their alkali metal, alkaline earth metal or ammonium salts. Suitable solvents are anhydrous aprotic solvents, such as aliphatic and aromatic hydrocarbons, cyclic and acyclic ethers, ketones, such as acetone and methyl ethyl ketone, nitriles, such as acetonitrile and propionitrile amides, such as dimethylformamide, and N-methylpyrrolidone and dimethyl sulfoxide. The reaction is also possible in 2-phase, aqueous-organic media—the above solvents may be used as organic solvents, provided that they are immiscible with water.

The reaction may be carried out at from $-30°$ to $+100°$ C., preferably from $0°$ to $80°$ C.

The compounds II may be manufactured from the corresponding alkyl sulfonamides by condensation with formic acid esters, in accordance with the following scheme:

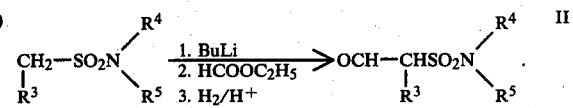

The compounds of the formula II may be isolated and used in pure form for manufacturing the phosphoric acid esters, but may also be phosphorylated in situ directly after manufacture, i.e., without being isolated.

The phosphorylation components are known and may be manufactured by processes described in the literature.

The new esters are non-distillable oils. In addition to elemental analysis, they are identified by their refractive index, and infrared and nmr data.

EXAMPLE 1

At $-5°$ C., 0.1 mole of BuLi as a 15% solution in n-hexane is dripped into a solution of 0.1 mole of methanesulfonic acid-N,N-di-methylamide in 75 ml of absolute tetrahydrofuran. 30 minutes after all has been added, 0.1 mole of ethylformate is introduced and the mixture is stirred at room temperature for 5 hours. Subsequently, 0.1 mole of O,O-diethylthiophosphoryl chloride is added and the mixture heated at 50° C. for 1 to 2 hours. After the solvent has been distilled off, the residue is dissolved in methylene chloride and washed twice with water. The residue remaining after concentration of the organic phase contains unreacted starting material, which is distilled off at 0.08 mbar. There is obtained 16 g of O,O-diethyl-O-(2-dimethylaminosulfonyl)-vinyl thiophosphate as a yellowish oil; $n_D^{25}$:1.4870.

The following compounds are obtained analogously:

reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus

| Example | $R^1$ | $R^2$ | X | $R^3$ | $R^4$ | $R^5$ | $n_D^{25}$ |
|---|---|---|---|---|---|---|---|
| 2 | $C_2H_5O$ | $n-C_3H_7S$ | S | H | $CH_3$ | $CH_3$ | 1.5047 |
| 3 | $C_2H_5O$ | $C_2H_5O$ | O | $CH_3$ | $CH_3$ | $CH_3$ | 1.4408 |
| 4 | $C_2H_5O$ | $n-C_3H_7S$ | S | $CH_3$ | $CH_3$ | $CH_3$ | 1.4980 |
| 5 | $C_2H_5O$ | $C_2H_5O$ | S | $CH_3$ | $CH_2-CH_2-O-CH_2$ | | 1.4812 |
| 6 | $C_2H_5O$ | $C_2H_5O$ | S | Cl | $CH_3$ | $CH_3$ | 1.4930 |
| 7 | $C_2H_5O$ | $n-C_3H_7S$ | S | Cl | $CH_3$ | $CH_3$ | 1.5128 |
| 8 | $C_2H_5O$ | $n-C_3H_7S$ | S | H | $CH_2-CH_2-O-CH_2-CH_2$ | | 1.5308 |
| 9 | $C_2H_5O$ | $C_2H_5O$ | S | H | " | | 1.5012 |
| 10 | $C_2H_5O$ | $C_2H_5O$ | O | H | $CH_3$ | $CH_3$ | 1.4608 |
| 11 | $C_2H_5O$ | $C_2H_5O$ | S | $CH_3$ | $CH_3$ | $CH_3$ | 1.4900 |
| 12 | $C_2H_5O$ | $C_2H_5O$ | S | H | $CH_3$ | ⬡ | 1.6325 |
| 13 | $C_2H_5O$ | $n-C_3H_2S$ | S | H | $CH_3$ | ⬡ | 1.5620 |
| 14 | $C_2H_5O$ | $C_2H_5O$ | S | H | $C_2H_5$ | $C_2H_5$ | 1.4860 |
| 15 | $C_2H_5O$ | $C_2H_5O$ | S | H | $C_2H_5$ | $C_2H_5$ | 1.5138 |
| 16 | $C_2H_5O$ | $C_2H_5O$ | O | H | $CH_3$ | ⬡ | 1.5065 |
| 17 | $C_2H_5O$ | sec.butS | S | $CH_3$ | $CH_3$ | $CH_3$ | 1.5175 |
| 18 | $CH_3O$ | $CH_3O$ | S | $CH_3$ | $CH_3$ | $CH_3$ | 1.4970 |
| 19 | $C_2H_5O$ | $C_2H_5O$ | S | $CH_3$ | $-(CH_2)_4-$ | | 1.5005 |
| 20 | $C_2H_5O$ | $C_2H_5O$ | O | $CH_3$ | $CH_2-CH_2-O-CH_2-CH_2$ | | 1.4740 |
| 21 | $C_2H_5O$ | $C_2H_5O$ | O | H | $-(CH_2)_4-$ | | 1.4848 |
| 22 | $C_2H_5O$ | i-butS | S | $CH_3$ | $CH_3$ | $CH_3$ | 1.5200 |
| 23 | $C_2H_5O$ | $C_2H_5O$ | S | $CH_3$ | $C_2H_5$ | $C_2H_5$ | 1.4835 |
| 24 | $C_2H_5O$ | $n-C_3H_7S$ | S | $CH_3$ | $C_2H_5$ | $C_2H_5$ | 1.5165 |
| 25 | $C_2H_5O$ | $i-C_4H_9S$ | S | Cl | $CH_3$ | $CH_4$ | |
| 26 | $C_2H_5O$ | $i-C_3H_7NH$ | O | Cl | $CH_3$ | $CH_3$ | |
| 27 | $C_6H_5O$ | $n-C_3H_7S$ | S | H | $CH_3$ | $CH_3$ | |
| 28 | $C_2H_5O$ | $i-C_3H_7NH$ | S | $CH_3$ | $CH_3$ | $CH_3$ | |
| 29 | $CH_3O$ | $CH_3O$ | S | $CH_3$ | $C_2H_5$ | $C_2H_5$ | |
| 30 | $C_2H_5$ | $C_2H_5O$ | O | $CH_3$ | $C_2H_5$ | $C_2H_5$ | 1.4510 |
| 31 | $C_2H_5$ | $i-C_3H_7NH$ | S | $CH_3$ | $C_2H_5$ | $C_2H_5$ | |
| 32 | $C_2H_5$ | $n-C_3H_7S$ | S | $CH_3$ | $C_2H_5$ | $C_2H_5$ | |
| 33 | $C_2H_5$ | $i-C_4H_9S$ | S | $CH_3$ | $C_2H_5$ | $C_2H_5$ | |
| 34 | $C_2H_5$ | sec.butNH | S | $CH_3$ | $CH_3$ | $CH_3$ | |
| 35 | $C_2H_5$ | i-butNH | S | $CH_3$ | $CH_3$ | $CH_3$ | |
| 36 | $CH_3$ | $CH_3O$ | S | H | $CH_3$ | $CH_3$ | |
| 37 | $C_2H_5$ | $i-C_3H_7NH$ | S | H | $CH_3$ | $CH_3$ | |
| 38 | $C_2H_5$ | $i-C_4H_9NH$ | S | H | $CH_3$ | $CH_3$ | |
| 39 | $CH_3$ | $CH_3O$ | S | H | $CH_2-CH_2-O-CH_2-CH_2$ | | |
| 40 | $C_2H_5$ | $i-C_3H_7NH$ | S | H | " | | |
| 41 | $CH_3$ | $CH_3O$ | S | $CH_3$ | " | | |
| 42 | $C_2H_5$ | $n-C_3H_7S$ | S | $CH_3$ | " | | |
| 43 | $CH_3$ | $CH_3O$ | S | $CH_3$ | $-(CH_2)_4-$ | | |
| 44 | $C_2H_5$ | $i-C_4H_9S$ | S | $CH_3$ | " | | |
| 45 | $C_6H_5$ | $n-C_3H_7S$ | S | H | $C_2H_5$ | $C_2H_5$ | |
| 46 | $C_2H_5$ | $i-C_3H_7NH$ | S | H | $C_2H_5$ | $C_2H_5$ | |
| 47 | $C_2H_5$ | $C_2H_5O$ | S | H | $n-C_3H_7$ | $n-C_3H_7$ | |
| 48 | $C_2H_5$ | $n-C_3H_7S$ | S | H | $n-C_3H_7$ | $n-C_3H_7$ | |
| 49 | $C_2H_5$ | $C_2H_5O$ | O | $CH_3$ | $n-C_3H_7$ | $n-C_3H_7$ | |
| 50 | $C_2H_5$ | $C_2H_5O$ | S | $CH_3$ | $n-C_3H_7$ | $n-C_3H_7$ | |
| 51 | $C_2H_5$ | $i-C_4H_9S$ | S | $CH_3$ | $n-C_3H_7$ | $n-C_3H_7$ | |
| 52 | $C_2H_5$ | $C_2H_5$ | S | $CH_3$ | $CH_3$ | $CH_3$ | |
| 53 | $C_2H_5$ | $C_2H_5$ | O | $CH_3$ | $CH_3$ | $CH_3$ | |
| 54 | $C_2H_5$ | $C_2H_5O$ | S | H | $-(CH_2)_6-$ | | |
| 55 | $C_2H_5$ | $C_2H_5O$ | S | $CH_3$ | $-(CH_2)_5-$ | | |

The compounds of the formula I according to the invention are suitable for effectively combating pests from the class of insects and mites. They are suitable as adulticides and ovicides.

Examples of injurious insects from the Lepidoptera order are Plutella maculipennis, Leucoptera coffeella, Hyponomeuta malinellus, Argyresthia conjugella, Sitotroga cerealella, Phthorimaea operculella, Capua pini, Thaumatopoes pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana,

*Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletix cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sericata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolli;* examples from the Isoptera order are *Reticulitermes lucifugus, Calotermes flavicollis, Leucotermes flavipes,* and *Termes natalensis.*

Examples from the Orthoptera order are *Forficula auricularia, Acheta domestica, Gryllotalpa gryllotalpa, Tachycines asynamorus, Locusta migratoria, Stauronotus marccoccanus, Schistocerca peregrina, Nomadacris stepemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The compounds according to the invention may be successfully used as pesticides for protecting crops, and in the hygiene sector, the protection of stored products, and the veterinary sector. They may be employed as contact and stomach poisons.

The active ingredients may be applied as such, in the form of formulations or ready-to-use preparations produced therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparations of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 3 parts by weight of compound no. 1 is intimately mixed with 97 parts by weight of particulate kaolin. A dust is obtained containing 3% by weight of the active ingredient.

II. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of compound no. 4 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of compound no. 6 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use preparations may vary within a wide range; it is generally from 0.0001 to 10%, preferably from 0.01 to 1%.

The active ingredients may also be successfully used in the ultra-low volume method, where it is possible to apply formulations containing more than 95 wt % of active ingredient, or even the 100% active ingredient.

There may be added to the active ingredients (if desired, immediately before use (tankmix) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methyl-thio)-propionaldehyde-O-(methylcarbamoyl)-oxime, S-methyl-N-[-(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphone-thioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methyl-thiophenyl)-phosphorothioate, O-ethyl-O-(3-methyl-4-methylthio-phenyl)-isopropyl-phosphoramidate, O,O-diethyl-O-[p-(methylsulfynyl)-phenyl]-phosphorothioate, O-ethyl-S-phenylethyl-phosphono-dithioate, O,O-diethyl-[2-chloro-1-(2,4dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethyl-thiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O- diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phen-oxybenzyl-α-isopropyl-4-chlorophenylacetate.

The biological action of the new compounds is illustrated in the following examples. The agent used for comparison purposes was phosphamidon.

EXAMPLE A

Contact action on cockroaches (*Blatta orientalis*)

The bottoms of 1 liter preserving jars are treated with acetonic solutions of the active ingredients. After the solvent has evaporated, 5 adult cockroaches are placed in each jar, and the kill rate is determined after 48 hours.

In this test, the compounds of Examples nos. 1, 3, 11, 14, 18 and 23 proved to have an action far superior to that of the comparative agent.

EXAMPLE B

Contact action on houseflies (*Musca domestica*)

Both covers and bottoms of Petri dishes 10 cm in diameter are lined with a total per dish of 2 ml of acetonic solutions of the active ingredients. After the solvent has evaporated, 10 flies are introduced into each dish. The kill rate is determined after 4 hours.

In this test, for example the compounds of Examples nos. 3, 11, 17, 18, 19, 20, 22, 23 and 24 have a far better action than the comparative agent.

EXAMPLE C

Breeding experiment with housefly larvae (*Musca domestica*)

50 g of a culture medium consisting of 10 parts of baker's yeast, 10 parts of dried milk, 100 parts of water and 1 part of agar is thoroughly mixed, while warm, with the aqueous active ingredient formulations. After the medium has cooled, approx. 0.1 ml of flies' eggs is placed on it and their development is observed for a week. The temperature is kept at 20° C.

In this test, for instance the compounds of Examples nos. 3, 4, 14, 15, 17, 18, 22, 23 and 24 are far superior to the comparative compound.

EXAMPLE D

Contact action on granary weevils (*Sitophilus granarius*)

Petri dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

In this test, for instance the compounds of Examples nos. 10, 14, 16 and 18 are far better than the comparative agent.

EXAMPLE E

Breeding experiment with *Drosophila melanogaster*

40 ml of a bran nutrient agar is introduced at 60° C. into plastic bottles (volume: 250 ml); 2 ml of the aqueous active ingredient formulations is then thoroughly mixed in. After having been allowed to cool, the nutrient agar is inoculated with a yeast suspension, and a rolled-up filter paper is placed to lean against the side of the bottle.

From 20 to 40 approximately 6-day old Drosophila are then introduced and the vessels capped.

Assessment takes place after 10 days.

In this test, for instance the compounds of Examples nos. 1, 4, 5, 6, 8 and 9 are far superior to the comparative compound.

We claim:

1. A phosphoric acid ester of the formula

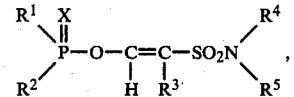

where $R^1$ is alkoxy of a maximum of 4 carbon atoms or phenyl, $R^2$ is alkyl or a maximum of 3 carbon atoms, alkoxy or alkylthio of a maximum of 4 carbon atoms, or alkylamino or dialkylamino, each alkyl being of a maximum of 4 carbon atoms $R^3$ is methyl, ethyl, hydrogen or chlorine, $R^4$ and $R^5$ are phenyl or alkyl of a maximum of 4 carbon atoms, or are, together with the nitrogen atom, a 5- to 7-membered heterocycle selected from the group consisting of pyrrolidine, morpholine, or oxazolidine and X is oxygen or sulfur, with the proviso that $R^1$ is not phenyl when $R^2$ is alkyl.

2. A pesticide comprising a pesticidally effective amount of at least one compound as set forth in claim 1 and a solid or liquid carrier.

3. A process for combating pests, wherein a pesticidally effective amount of at least one compound of the formula I as set forth in claim 1 is allowed to act on the pests or their eggs.

4. A phosphoric acid ester as set forth in claim 1, wherein $R^1$ is methoxy, ethoxy or phenyl, $R^2$ is methoxy, ethoxy, n-propylthio, isobutylthio, sec-butylthio, methylamino, dimethylamino or isopropylamino, $R^3$ is hydrogen, chlorine or methyl, $R^4$ and $R^5$ are methyl, ethyl, or formed with the nitrogen atom a pyrrolidine or morpholine ring.

* * * * *